United States Patent
Woo et al.

(10) Patent No.: US 9,857,239 B2
(45) Date of Patent: *Jan. 2, 2018

(54) TEMPERATURE ANALYSIS WITH VOLTAGE-CURRENT TIME DIFFERENTIAL OPERATION OF ELECTROCHEMICAL SENSORS

(71) Applicants: EmiSense Technologies, LLC, Ladera Ranch, CA (US); Lawrence Livermore National Security, LLC, Livermore, CA (US)

(72) Inventors: Leta Yar-Li Woo, Oakland, CA (US); Robert Scott Glass, Livermore, CA (US); Joseph Jay Fitzpatrick, Glendale, CA (US); Gangqiang Wang, Salt Lake City, UT (US); Brett Tamatea Henderson, Salt Lake City, UT (US); Anthoniraj Lourdhusamy, West Jordan, UT (US); James John Steppan, Park City, UT (US); Klaus Karl Allmendinger, San Juan Capistrano, CA (US)

(73) Assignees: Lawrence Livermore National Security, LLC, Livermore, CA (US); EmiSense Technologies, LLC, Ladera Ranch, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/444,427

(22) Filed: Feb. 28, 2017

(65) Prior Publication Data

US 2017/0234743 A1    Aug. 17, 2017

Related U.S. Application Data

(62) Division of application No. 14/055,562, filed on Oct. 16, 2013, now Pat. No. 9,581,564.

(51) Int. Cl.
*G01K 13/02* (2006.01)
*G01N 27/407* (2006.01)
(Continued)

(52) U.S. Cl.
CPC ......... *G01K 13/02* (2013.01); *G01N 27/4065* (2013.01); *G01N 27/4071* (2013.01);
(Continued)

(58) Field of Classification Search
CPC .......... G01N 27/4071; G01N 27/4065; G01N 33/0037; G01K 13/02; G01K 2205/04; G01K 2013/024
(Continued)

(56) References Cited

U.S. PATENT DOCUMENTS

| | | |
|---|---|---|
| 6,488,836 B1 | 12/2002 | Nakata et al. |
| 2004/0149008 A1* | 8/2004 | Allmendinger ...... G01N 27/419 73/23.31 |

(Continued)

OTHER PUBLICATIONS

"Supplementary European Search Report for Application No. EP14853912" dated May 24, 2017, 10 pages.
(Continued)

*Primary Examiner* — Shogo Sasaki
(74) *Attorney, Agent, or Firm* — Kunzler, PC (57) ABSTRACT

A method for temperature analysis of a gas stream. The method includes identifying a temperature parameter of an affected waveform signal. The method also includes calculating a change in the temperature parameter by comparing the affected waveform signal with an original waveform signal. The method also includes generating a value from the calculated change which corresponds to the temperature of the gas stream.

12 Claims, 8 Drawing Sheets

(51) Int. Cl.
*G01N 27/406* (2006.01)
*G01N 33/00* (2006.01)

(52) U.S. Cl.
CPC ..... *G01N 27/4074* (2013.01); *G01N 27/4075* (2013.01); *G01N 33/0037* (2013.01); *G01K 2013/024* (2013.01); *G01K 2205/04* (2013.01)

(58) Field of Classification Search
USPC .......................................................... 205/775
See application file for complete search history.

(56) References Cited

U.S. PATENT DOCUMENTS

| | | | | |
|---|---|---|---|---|
| 2005/0077177 | A1* | 4/2005 | Sakayanagi | G01N 27/419 204/425 |
| 2005/0098449 | A1* | 5/2005 | Ochs | G01N 31/005 205/781 |
| 2006/0082252 | A1* | 4/2006 | Allmendinger | F02D 41/2096 310/316.03 |
| 2007/0261475 | A1* | 11/2007 | Allmendinger | G01N 27/419 73/31.01 |
| 2009/0145778 | A1* | 6/2009 | Allmendinger | G01N 27/419 205/789 |

OTHER PUBLICATIONS

Miura et al. "Impedancemetric Gas Sensor Based on Zirconia Solid Electrolyte and Oxide Sensing Electrode for Detecting Total NOx at High Temperature" Sensors and Actuators B: Chemical: International Journal Devoted to Research and Development of Physical and Chemical Transducers, (Aug. 1, 2003), pp. 221-228.

Rheaume et al. "A Review of Recent Progress in Sensing of Gas Concentration by Impedance Change" Ionics, vol. 17, No. 2, (Jan. 13, 2011), pp. 99-108.

Shogo "Non-Final Office Action for U.S. Appl. No. 15/444,416" dated May 19, 2017, 21 pages.

Shogo "Non-Final Office Action for U.S. Appl. No. 15/444,420" dated May 19, 2017, 19 pages.

* cited by examiner

TEMPERATURE ANALYSIS WITH VOLTAGE-CURRENT TIME DIFFERENTIAL OPERATION OF ELECTROCHEMICAL SENSORS

CROSS-REFERENCE TO RELATED APPLICATIONS

This application is a divisional of U.S. application Ser. No. 14/055,562, now U.S. Pat. No. 9,581,564, filed on Oct. 16, 2013, which is incorporated by reference herein in its entirety.

STATEMENT OF FEDERALLY SPONSORED RESEARCH

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Increasingly stringent emissions regulations require automobile manufacturers to develop comprehensive on-board diagnostic (OBD) systems for exhaust gas monitoring. Compact, inexpensive sensors are particularly in demand for monitoring and control of regulated pollutants including hydrocarbons, carbon monoxide, and oxides of nitrogen ($NO_x$). Sensors for these applications have been proposed based on semiconducting oxides, heterocontacts in semiconducting oxides, surface acoustic waves, and capacitance. Other sensors are based on solid-state electrochemical devices, which typically use a solid ceramic electrolyte attached with two or more metal or metal-oxide electrodes and operate in either potentiometric (open circuit) or amperometric (DC-biased) modes.

Significant progress has been made towards the development of deployable sensors using yttria-stabilized zirconia (YSZ) as the electrolyte of solid-state electrochemical devices. However, there still exist significant shortcomings related to stability, sensitivity, response time, and cross-sensitivity. These shortcomings are responsible for only one type of $NO_x$ sensor being available commercially to date. The commercially available amperometric $NO_x$ sensors are not ideal for widespread use due to high cost, complexity, and limited performance. The benchmark sensor is the well-known YSZ-based oxygen sensor currently used in almost all automobiles. Although that sensor demonstrates the commercial feasibility of this technology, it addresses a task that is less complicated than low concentration (ppm level) gas sensing used in $NO_x$ applications.

Some approaches for solid-state electrochemical sensors use frequency-domain impedancemetric modes of operation. This approach relies on specific material compositions and microstructures to maximize the sensor response at higher frequencies, because higher frequencies allow for faster sampling rates and improved signal-to-noise ratios. This approach also relies on the measurement of the phase angle as a metric for monitoring the gas concentration.

SUMMARY

Embodiments of the invention relate to a device for signal processing. The device includes a signal generator, a signal detector, and a processor. The signal generator generates an original waveform. The signal detector detects an affected waveform. The processor is coupled to the signal detector. The processor receives the affected waveform from the signal detector. The processor also compares at least one portion of the affected waveform with the original waveform. The processor also determines a difference between the affected waveform and the original waveform. The processor also determines a value corresponding to a unique portion of the determined difference between the original and affected waveforms. The processor also outputs the determined value.

Embodiments of the invention relate to a system for analysis of a gas stream. The system includes a signal generator, an electrochemical sensor, a signal detector, and a processor. The signal generator generates an original waveform. The electrochemical sensor receives the original waveform. The electrochemical sensor is disposed at least partially within the gas stream. The electrochemical sensor includes a first electrode and a second electrode. The second electrode is disposed relative to the first electrode. The signal detector detects an affected waveform from the electrochemical sensor. The processor is coupled to the signal detector. The processor receives the affected waveform from the signal detector. The processor also compares at least one portion of the affected waveform with the original waveform. The processor also determines a difference between the affected waveform and the original waveform. The processor also determines a value corresponding to at least one characteristic of the gas stream based on a unique portion of the determined difference between the original and affected waveforms. The processor also outputs the determined value corresponding to the at least one characteristic of the gas stream.

Embodiments of the invention relate to a method for analysis of a gas stream. The method includes identifying an affected region of an affected waveform signal corresponding to at least one characteristic of the gas stream. The method also includes calculating a difference between the affected region of the affected waveform signal and a corresponding region of an original waveform signal. The affected region and the corresponding region of the waveform signals have a sensitivity specific to the at least one characteristic of the gas stream. The method also includes generating a value for the at least one characteristic of the gas stream based on the calculated difference.

Embodiments of the invention relate to a method for temperature analysis of a gas stream. The method includes identifying a temperature parameter of an affected waveform signal. The method also includes calculating a change in the temperature parameter by comparing the affected waveform signal with an original waveform signal. The method also includes generating a value from the calculated change which corresponds to the temperature of the gas stream.

BRIEF DESCRIPTION OF THE DRAWINGS

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments facilitate the detection of pollutant gases in a hot, flowing gas stream. In the course of investigating frequency-domain impedancemetric modes of operation, a surprising discovery occurred when employing inexpensive digital electronics to monitor the voltage-current differential in the time-domain. A source wave was applied to a sensor that was subjected to a gas stream, and a corresponding response wave was obtained. The source and response waves exhibited similar peak-to-peak values indicating that no phase angle shift or phase angle difference occurred.

In contrast, previous impedancemetric modes of operation in the frequency-domain used expensive electrochemical equipment that indicated phase angle changes. Nevertheless, the distortion of the response wave in the low-cost digital electronics did result in a time-voltage differential at the zero-crossing, as well as at non-zero magnitudes.

Furthermore, using the time-voltage differential in the time-domain allowed for larger amplitude signals indicating the potential for higher sensitivity toward $NO_x$ and lower constraints for specified material compositions and microstructures to achieve different levels of performance. Thus, it was discovered that the use of time-voltage differentials in the time-domain allows for more sensor design flexibility.

A digital method for operating embodiments of solid-state electrochemical gas sensors using time-domain measurements may have advantages over conventional direct current (DC) methods such as potentiometric and amperometric sensors, as well as other alternating current (AC) methods such as frequency-domain impedancemetric sensors.

In some embodiments, the applied signal is an AC waveform. The applied signal may be any type of symmetrical or asymmetrical AC waveform. In some examples, particular waveforms such as sinusoidal or triangular waveforms may be applied. In some embodiments, alternate waveform shapes (i.e., other than a sinusoidal waveform) may produce larger response signals.

In some embodiments, the response of the solid-state electrochemical gas sensor is digitally measured as a voltage-current time differential as indicated by the time domain zero-crossing. In other embodiments, the voltage-current time differential is monitored at another specified non-zero magnitude. In some embodiments, measurement of the voltage-current time differential at specific points of magnitude other than the zero-crossing produces larger signals. Additionally, the application of a particular type of waveform, or a waveform with specific characteristics, may influence the sensitivity or other characteristic of the response signal that is detected. For example, in some embodiments, the application of a triangular waveform may result in high sensitivities and large sensor signals.

In some embodiments, the digital time-domain method can be used for simultaneous measurement of multiple gas species and/or environmental variations such as temperature. For example, in a single wave cycle, the system is capable of measuring multiple species of gases within an exhaust stream. As another example, the detection of part-per-million (ppm) levels of $NO_x$ (e.g., NO and $NO_2$) as well as temperature in automotive exhaust may be done through the application of both triangular and sine waveforms. In another example, asymmetric signals and multiple voltage-current time differentials can be used to extract measurements of multiple gas species simultaneously. In yet another example, combining changes in source wave frequency can be used to extract temperature information of the sensor and/or the gas stream.

In further embodiments, certain material and design features can be identified specifically for detecting $NO_x$ using a solid-state electrochemical sensor that are based on reaction mechanisms responsible for sensing. However, the potential applications for the embodiments described herein are significantly broader in terms of the types of gas species that can be detected (e.g., oxygen, nitrogen dioxide, hydrocarbons, etc.) and are also not necessarily limited to solid-state electrochemical gas sensors.

Development of this technology is of interest to various vehicle technologies. And embodiments of this technology have primary, short-term applications for on-board monitoring of vehicle (especially diesel) emissions. However, while many embodiments described herein specifically refer to the monitoring of industrial exhaust gases and vehicle emissions, broader applications are available in any area where electrochemical sensors are of interest. For example, some embodiments described herein may be employed in medical, health & safety, and environmental applications.

Figure 1:
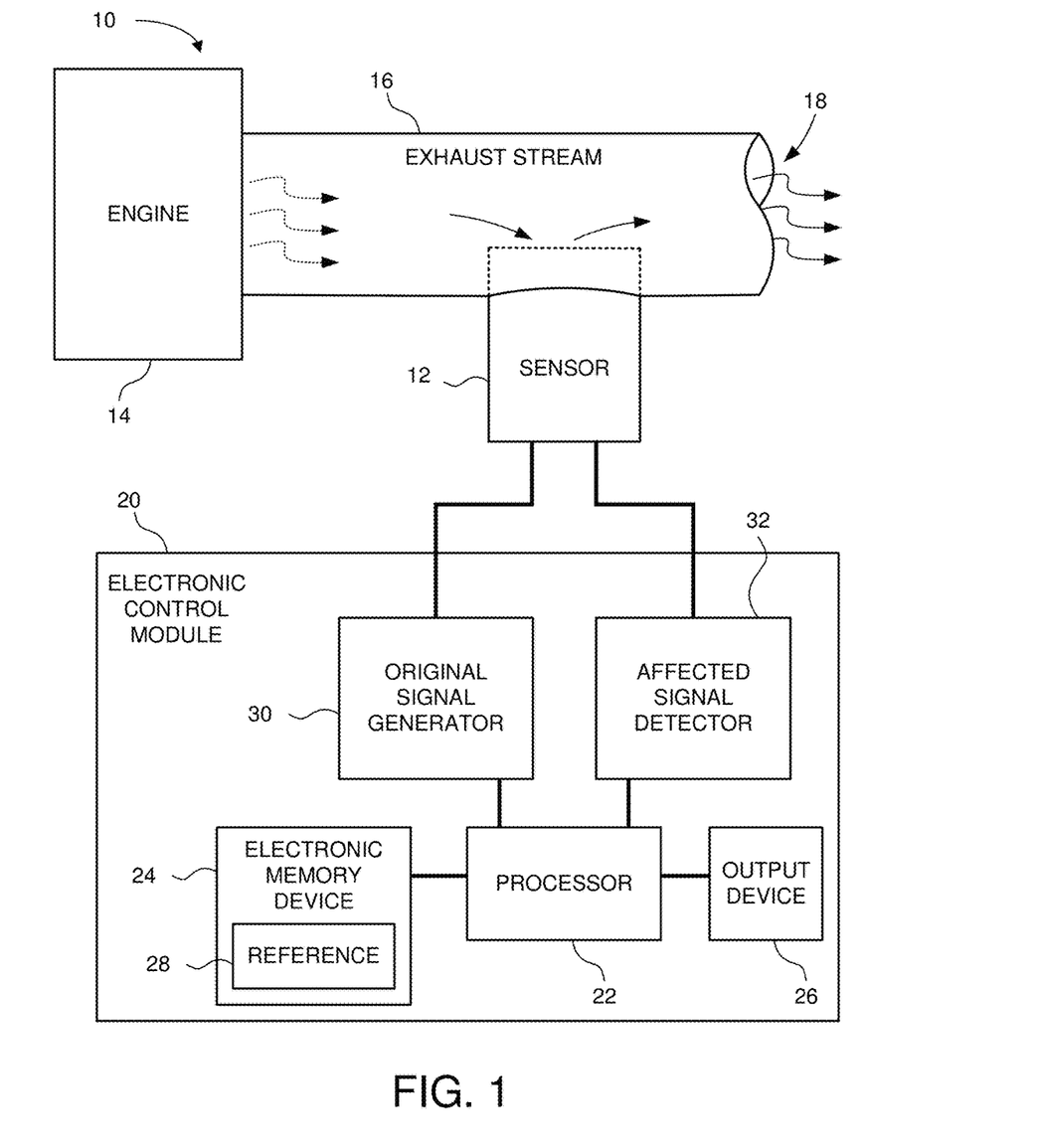
FIG. 1 depicts a schematic block diagram of one embodiment of an exhaust sensor system.

FIG. 1 depicts a schematic block diagram of one embodiment of an exhaust sensor system 10. The illustrated exhaust sensor system 10 includes a sensor assembly 12, an engine 14, and an exhaust system 16. The engine 14 produces exhaust which moves through the exhaust system 16. The exhaust system 16 facilitates flow of the exhaust gases to a gas outlet 18, typically for emission into the atmosphere. The sensor assembly 12 is at least partially inserted into the exhaust system 16 to detect a parameter within the exhaust stream. As the gas in the exhaust system 16 passes over and/or through the sensor assembly 12, the sensor assembly 12 detects a condition within the exhaust by measuring chemicals or temperature or other parameters at the sensor assembly 12, as described herein. In one embodiment, the sensor 12 is a single cell sensor without a separate reference cell. A single cell arrangement may be beneficial in certain applications. For example, a single cell includes a pair of electrodes and an electrolyte. Such a single cell system might reduce the complexity and requirements of the system as well as reduce cost of materials and components. In another embodiment, the system 10 includes a reference cell (not shown) mounted outside of the exhaust system. This may be beneficial in certain applications. For example, in some applications, this may allow the system 10 to achieve a higher degree of sensitivity with reduced margins of error. In a specific embodiment, the sensor assembly 12 includes a $NO_x$ sensor to detect conditions related to the presence of NO and/or $NO_2$ within the exhaust stream. However, other embodiments may be implemented to detect other chemicals or compositions within the exhaust stream.

The exhaust sensor system 10 also includes an electronic control module 20. The electronic control module 20 includes a processor 22, an electronic memory device 24, and an output device 26. In some embodiments, the electronic memory device 24 stores one or more references 28 and/or other data, as described herein. The electronic control module 20 also includes an original signal generator 30 and a response signal detector 32.

In further embodiments, the electronic control module 20 also may include a control circuit (not shown) to control some or all of the operations of the sensor assembly 12. Alternatively, some or all of the control circuit functionality may be implemented at the sensor assembly 12 or at another location that is not necessarily proximate the electronic control module 20. Additionally, in some embodiments, the control circuit may control a peripheral system (not shown). Some examples of peripheral systems that may be implemented at the sensor assembly 12 include, but are not limited to, a heater (not shown) or a chemical neutralizer system (not shown). Instead of or in addition to the chemical neutralizer system, some embodiments may include an emission control element (not shown) to neutralize other aspects of the chemicals and/or substances within the exhaust system, either upstream or downstream from the sensor assembly 10. In other embodiments, the control circuit may control peripheral systems at other locations within the exhaust sensor system 10.

In some embodiments, reference 28 is an algorithm into which data is entered by the processor to generate a value corresponding to some characteristic of the exhaust stream. In other embodiments, the reference 28 is a lookup table to correlate a sensor signal to a value for a characteristic of the exhaust stream. In some embodiments, the value corresponds to one or more concentrations of gases within the exhaust stream. In another embodiment, the value corresponds to a temperature of the exhaust stream. In other embodiments, the value corresponds to other characteristics of the exhaust stream.

Figure 2A:
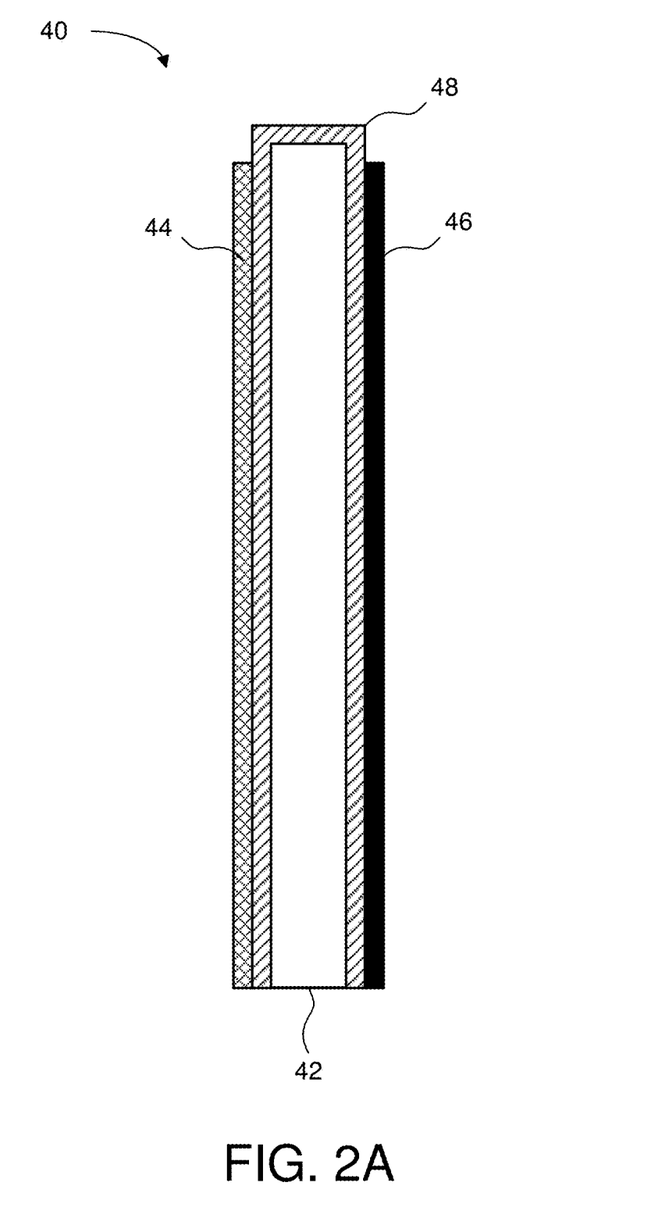
FIG. 2A depicts a schematic diagram of one embodiment of a gas sensor for use in the sensor assembly of FIG. 1.

In one embodiment, the sensor assembly 12 includes a solid-state electrochemical gas sensor (refer to FIG. 2). Other embodiments of the sensor assembly 12 may include different types of gas sensors.

The processor 22 communicates with the original signal generator 30 to apply an original signal to the gas sensor of the sensor assembly 12. The input waveform may be any type of symmetrical or asymmetrical alternating current (AC) input waveform. Additionally, the input waveform may have one or more known characteristics such as frequency, amplitude, or another similar identifier. In a particular example, the application of a triangular input waveform may result in higher sensitivities and larger sensor signals compared with the application of a sinusoidal input waveform. This is similar to improved results that can be obtained using the time-domain response compared with the phase angle measurements using frequency-domain (i.e., impedancemetric) techniques. In some embodiments, the superior response signal for detection of gas species using the triangular waveform in the time-domain may be related to the wave distortions that are a result of how gas composition influences electrochemical reactions. Additionally, the wave distortions in the time-domain may allow for higher resolution (and thus higher sensitivities and larger sensor signals) when compared with measurements made in the frequency-domain (i.e., impedancemetric methods).

In some embodiments, the original signal generator 30 is controlled to generate and apply different types of input waveforms over time. Accordingly, one or more of the waveform characteristics, or the type of waveform, changes over time. Such changes may be controlled in a dynamic manner by the processor 22 to occur abruptly or over a defined amount of time.

In response to the input waveform applied to the sensor assembly 12, the response signal detector 32 detects a time-domain response that is at least partially dependent on the input waveform and any waveform alterations resulting from the composition of the gas in the exhaust stream. In other words, one or more characteristics of the gas in the exhaust stream may cause time-domain changes to the response waveform relative to the input waveform. For example, the time-domain response may be influenced by the presence of NO and/or $NO_2$ in the gas stream. The processor 22 may identify these changes and, consequently, identify one or more corresponding characteristics of the gas stream. In one embodiment, the response of the solid-state electrochemical gas sensor is digitally measured as a voltage-current time differential as indicated by either the time domain zero-crossing, at another specified non-zero magnitude, or at some combination of magnitudes. The response obtained by the response signal detector 32 is then presented to the processor 22 for further use such as data storage and/or reporting via the output device 26.

In addition to detecting the presence and/or concentration of gas species within the gas stream, some embodiments facilitate detection of temperature fluctuations of the gas stream and/or sensor assembly 12. Certain input waveforms may result in response waveforms that are primarily or solely responsive to temperature changes and do not respond (or only respond trivially) to changes in gas concentration. For example, a low-amplitude, high-frequency sine wave has reduced sensitivity to gas species but measurable sensitivity to temperature. Other wave forms with other characteristics may be more or less sensitive to gas species and temperatures. For example, a triangle waveform is capable of providing a measurement of temperature as well as demonstrating a sensitivity to gas species.

Such a waveform may be generated intermittently to measure temperature and adjust the input waveform. In some embodiments, adjustment of the input waveform may improve the accuracy of the measurement of certain gas species. For example, some testing has shown as low as a 1.6 ppm margin of error in measurement of $NO_x$ concentrations around 200 ppm and 10% $O_2$.

In some embodiments, the processor 22 may implement feedback from the response signal detector 32 to the original signal generator 30. For example, the processor 22 may direct the original signal generator 30 to modify the frequency and/or shape of the input waveform to identify temperature fluctuations directly so that the measured fluctuations could then be used to adjust the overall sensor signal and improve accuracy.

In further embodiments, the detection of temperature may be sequentially arranged with the detection of gas species. For example, a triangular input waveform may be used to detect gas species, and then a sinusoidal input waveform with higher frequency and lower amplitude may be used to determine temperature. In a more specific example, the signal for $NO_x$ is obtained using a triangular input waveform with 100 mV amplitude and 50 Hz frequency. Then the triangular input waveform is briefly interrupted with a signal that can be used to identify temperature variations using a sine waveform with 50 mV amplitude and 10 kHz frequency. In other embodiments, other types of simultaneous and/or sequential measurement schemes may be employed to measure any number of characteristics of the gas stream.

FIG. 2A depicts a schematic diagram of one embodiment of a gas sensor 40 for use in the sensor assembly of FIG. 1. The illustrated gas sensor 40 includes a substrate 42, a plurality of electrodes 44 and 46, and an electrolyte 48. In some embodiments, at least one of the plurality of electrodes 44 and 46 includes a sensing material such as pure gold, gold-based alloys, or doped lanthanum-based perovskites (such as strontium-doped lanthanum manganite [LSM]). In other embodiments, one of the plurality of electrodes 44 and 46 includes one of the materials listed above while the other of the plurality of electrodes 44 and 46 includes a non-sensing material (such as platinum, platinum-based alloys, or other electrically conductive metal alloy compositions). In some embodiments, the electrolyte 48 includes an ionically conducting material. For example, the electrolyte 48 may include yttria-stabilized zirconia (YSZ). In some embodiments, the substrate 42 is an electrically insulating material. For example, the substrate 42 may include alumina ($Al_2O_3$). In some embodiments, the substrate 42 contains an embedded resistive heater with a Pt-based allow composition. For convenience electrical leads are not shown.

In some embodiments, the sensor design may be symmetric with the electrodes 44 and 46 made of the same material or substantially the same material. In other embodiments, the sensor design may be asymmetric with the electrodes 44 and 46 made of different materials. Although the time-domain methods described herein are effective for symmetric sensor designs and geometries, in some embodiments the wave distortions in the time-domain are more pronounced and exaggerated for sensor designs and geometries involving asymmetric electrodes.

For example, the asymmetric electrodes may lead to large differences in reaction rates at each of the electrodes in the presence of oxygen and $NO_x$. In particular, when platinum (a good oxygen catalyst with fast reaction rates) is used as one electrode, and gold is used as the other electrode, the wave distortions may be more pronounced than with a symmetric design or with some other asymmetric materials. In some embodiments, the asymmetric wave distortions also allow larger sensor signals to be extracted at specified points beside the typical zero-crossing. Thus, the choice of the specific point of magnitude to produce the larger signal may rely on the specific sensor design and geometry for measurements of a particular composition.

In some embodiments, an asymmetric sensor design used within the digital time-domain can also facilitate simultaneous measurement of multiple gas species. As an example, the response waveform may have asymmetrical properties which can be attributed to two electrodes with different compositions (e.g., platinum and gold). The asymmetrical properties of the response waveform may lead to portions of the waveform that are dominated by one gas species compared to other portions of the waveform that have a weak dependence. In this way, specific regions of the waveform with large differences in response to a specific gas can be used to emphasize and/or isolate the contribution of the gas species. For example, in some embodiments the oxygen response can be isolated from the changes in $NO_x$ by "tuning" the measurement to different regions of the waveform that exhibit either a very large response or a minimal response to oxygen as compared to $NO_x$. As used herein, tuning refers to identifying characteristics associated with a particular time and/or magnitude of the waveform. Therefore, the asymmetric signals and multiple voltage-current time differentials can be used to extract measurements of multiple gas species simultaneously. In further embodiments, other gas species that are potential interferents, such as ammonia, also may be detected using this same methodology.

Figure 2B:
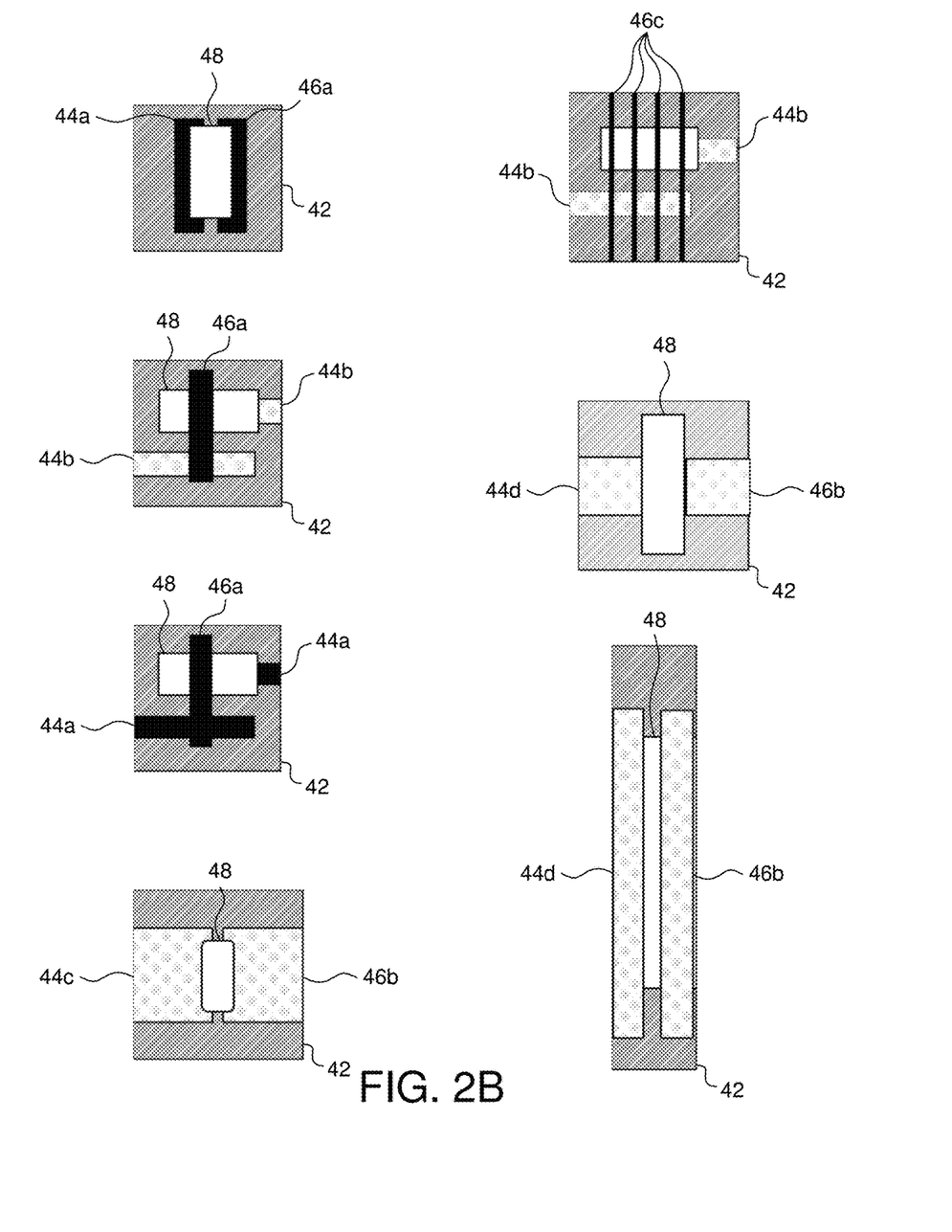
FIG. 2B depicts multiple embodiments of sensor arrangements.

FIG. 2B depicts multiple embodiments of sensor arrangements. The depicted embodiments include several arrangements and material options for various components. In particular, some of the embodiments include an YSZ electrolyte 48, dense strontium-doped lanthanum manganite (LSM) electrodes 44a and 46a, and an alumina substrate 42. Some embodiments include asymmetric combinations of electrodes by combining Pt electrode 44b with dense LSM electrode 46a. Other embodiments include gold-based alloy electrodes 44c and 46b. Another embodiment includes gold wire electrodes 46c with platinum electrodes 44b. Other embodiments may include other arrangements and material selections for each component.

Figure 3A:
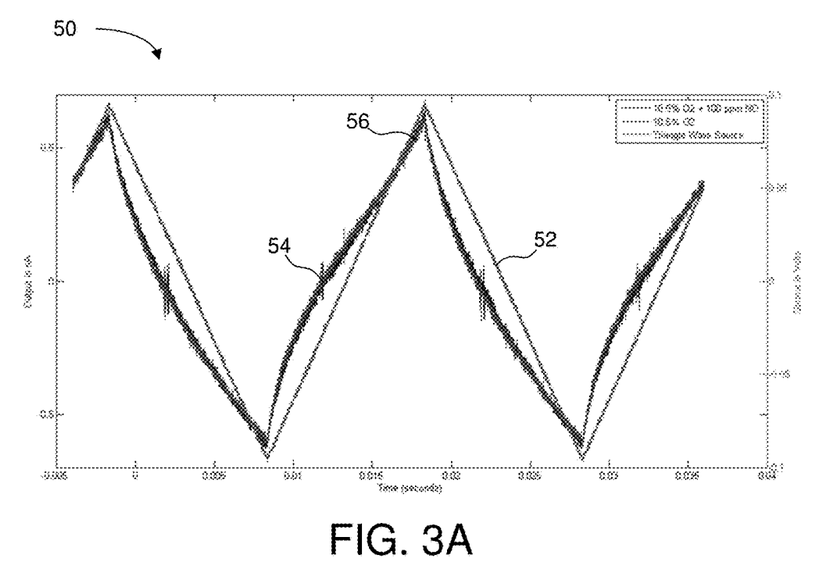
FIG. 3A depicts one embodiment of a waveform diagram of a triangular input waveform and corresponding response waveform regions.

FIG. 3A depicts one embodiment of a waveform diagram 50 of an original triangular input waveform 52 and corresponding response waveform regions 54 and 56. The input waveform 52 is representative of the input waveform generated by the input waveform generator 30 and applied to the sensor assembly 12. The response waveform regions 54 and 56 are representative of response waveforms detected by the response waveform detector 32. In one embodiment, a voltage is input to the sensor 12 and a current is returned and measured. Other forms of original and affected signals are also useful.

In depicted embodiment, the input waveform 52 is a voltage signal measured in Volts as shown on the right-hand vertical axis. The affected waveform with regions 54 and 56 is superimposed over the original input waveform 52 and is a current signal measured in nA as shown on the left-hand vertical axis. Each waveform is plotted relative to time as shown on the horizontal axis.

In this example, the response waveform regions 54 and 56 represent current measured through the cell. The current oscillates back and forth centered at a zero. The change in the general curve at the response waveform region 54 corresponds to a sensitivity to $O_2$ while the response waveform region 56 corresponds to a sensitivity to $O_2$ and NO. Without the $O_2$ sensitivity at region 56, the curve would more closely resemble the falling portion of the waveform without the flattened portion at region 56. Other portions of the waveform may demonstrate sensitivities to other species of gas.

Figure 3B:
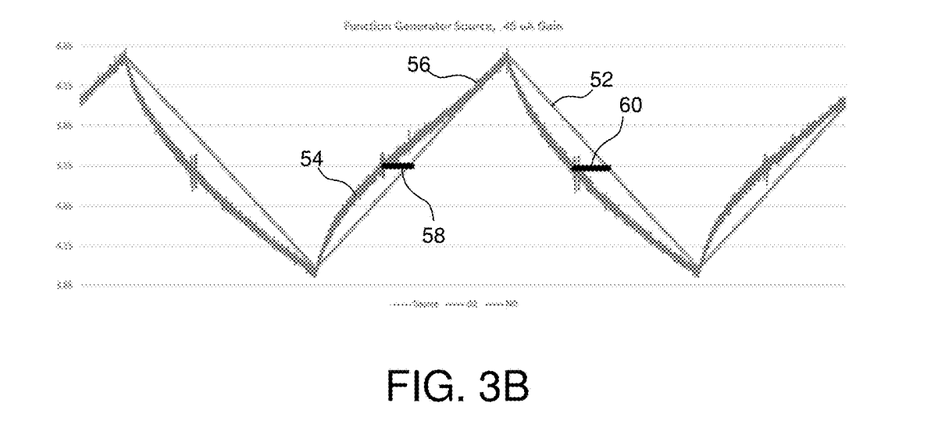
FIG. 3B depicts waveforms similar to the waveforms of FIG. 3A with additional markings to indicate time gaps between 0A and 0V on both sides of the waveform.

FIG. 3B depicts similar waveforms to the waveforms of FIG. 3A with additional markings 58 and 60 to indicate time gaps between 0A and 0V on both sides of the waveform. The plot of FIG. 3B has an offset of 5.1 xV for sensor ground. The markings 58 and 60 correspond to the combined effect of $NO_x$ and $O_2$, which is not evenly distributed over the entire waveform. By measuring the time gaps between the original signal 52 and the affected signal with regions 54 and 56 on both the rising and falling sides of the waveform and combining them, it is possible to get a much bigger signal for the gas species as compared with conventional phase-shift measurements.

Although FIGS. 3A and 3B use triangular waveforms, other embodiments may use other types of waveforms. For example, similar results may be achieved using sinusoidal waveforms. However, in some embodiments, the response may be smaller or a different magnitude compared with the response obtained using triangular waveforms.

Figure 3C:
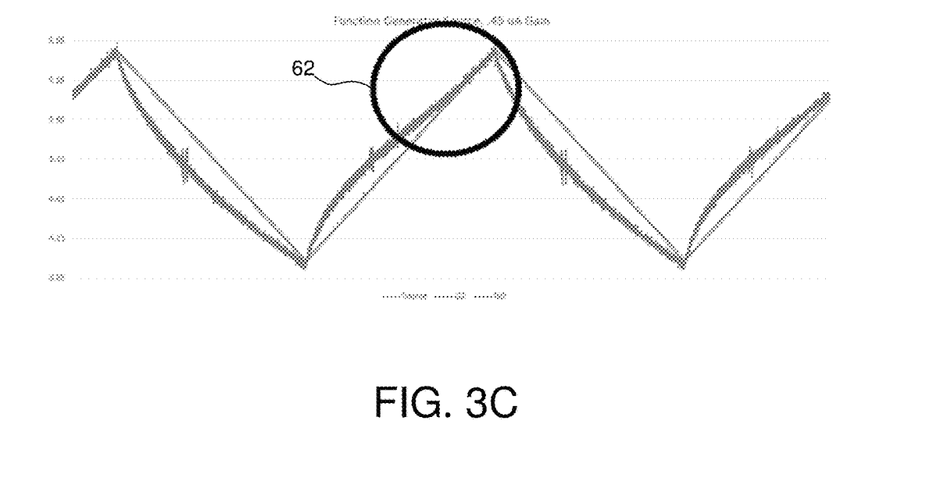
FIG. 3C depicts the waveforms of FIG. 3B with an emphasis on a portion of the triangular waveforms.

FIG. 3C depicts the waveforms of FIG. 3B with an emphasis 62 on a portion of the triangular waveforms. The emphasized 62 region demonstrates a sensitivity to $O_2$. The sensitivity is demonstrated by the flattening of the curve in the emphasized 62 region. This results from a reversal in the polarity of the affected signal due to the presence of $O_2$ (discussed further below with reference to FIG. 3D).

Figure 3D:
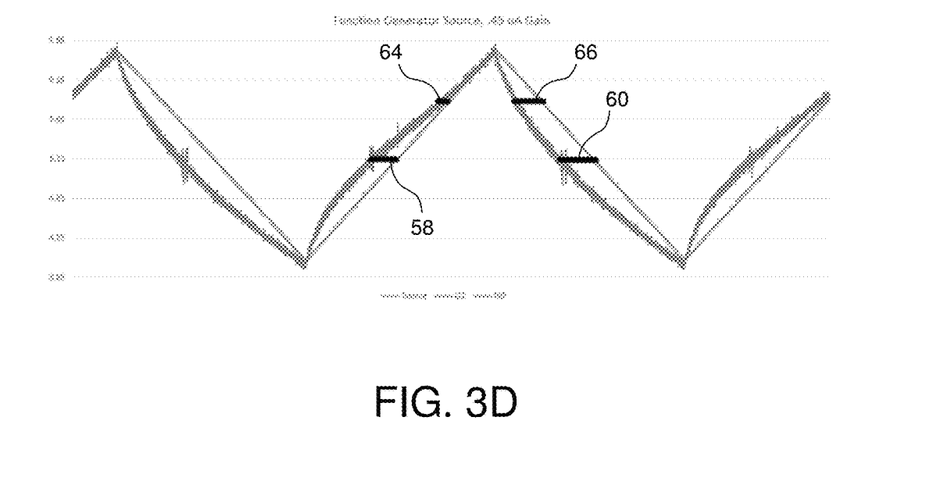
FIG. 3D depicts the waveforms of FIG. 3B with the markings of FIG. 3B and additional markings at non-zero crossings.

FIG. 3D depicts the waveforms of FIG. 3B with the markings 58 and 60 of FIG. 3B and additional markings 64 and 66 at non-zero crossings. By measuring the differential signals in two places, it can be seen that the effect and direction of the NO response is the same for all measurements, but the effect and direction of the $O_2$ response is to reverse polarity between measurements 58 and 64. In one example, the voltage-current time differential signals are obtained at the zero crossings (see markings 58 and 60) and at approximately 60% of the peak voltage in one polarity (see markings 64 and 66). When the signals are calibrated, the $O_2$ signals detected at 60% (64 and 66) can be calculated and then subtracted out of the cumulative measurement taken at the zero crossing (58 and 60). The remaining signal can be used to extract NO.

Figure 3E:
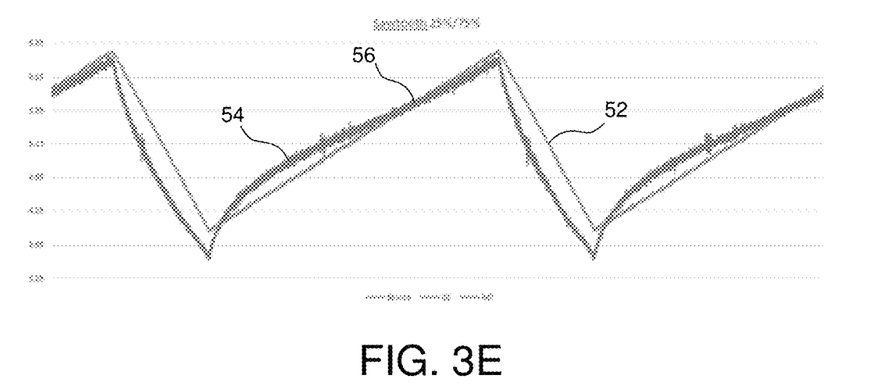
FIG. 3E depicts a sawtooth input waveform with corresponding response waveform regions.

FIG. 3E depicts a sawtooth input waveform 52 with corresponding response waveform regions 54 and 56. Each of regions 54 and 56 are similar to regions 54 and 56 as shown in FIG. 3A. However, FIG. 3E illustrates the response regions as generated with input 52 as a sawtooth waveform. In the illustrated embodiment, the sawtooth waveform exhibits an interesting phenomenon when the current leads the voltage at response region 56. The reversal in polarity due to the presence of $O_2$ in the exhaust stream pushes the current ahead enough to actually lead voltage in the time domain. This further illustrates how certain waveforms demonstrate sensitivities, at certain regions, to certain gas species within the exhaust stream.

In further embodiments, it is possible to extract gas species measurements based on the response waveform resulting from alternating input waveforms. For example, by using an asymmetric sawtooth input waveform, and alternating the direction of the asymmetry, the dominant gas species effect can be measured separately with each alternating waveform. In some embodiments, the use of asymmetric, alternating input waveforms may yield more accurate measurements for certain gas species. Measurements for temperature and other characteristics of the exhaust stream may also be taken by alternating input waveforms specific to measurement of that species or characteristic.

Figure 3F:
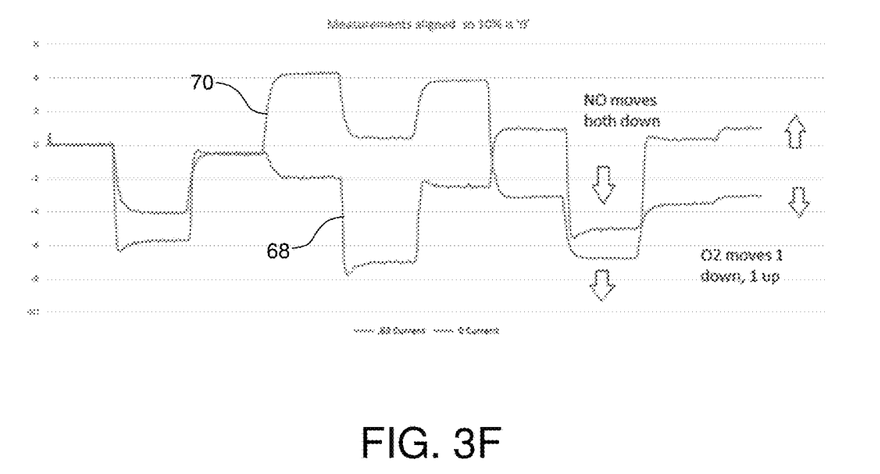
FIG. 3F depicts an embodiment of response signals corresponding to varied gas species concentrations.

FIG. 3F depicts an embodiment of response signals corresponding to varied gas species concentrations. While FIGS. 3A-E depict results gathered from steady-state experiments, FIG. 3F demonstrates results gathered with variations in gas species concentrations. FIG. 3F illustrates the effect of NO and $O_2$ on the sensor output. In particular, NO appears to constantly move the signal downward while $O_2$ has tendencies to reverse the polarity of the signal in certain regions.

Figure 4:
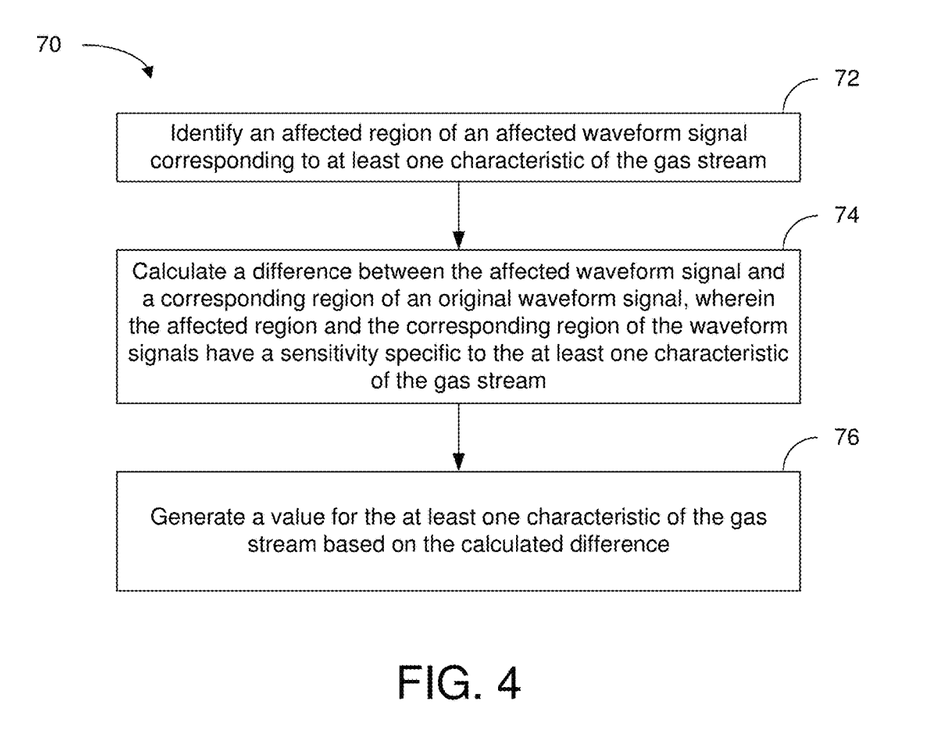
FIG. 4 depicts one embodiment of a flow chart diagram of a method for measuring gas species using voltage-current differential in the time-domain.

FIG. 4 depicts one embodiment of a flow chart diagram of a method 70 for measuring gas species using voltage-current differential in the time-domain. The method includes identifying 72 an affected region of an affected waveform signal corresponding to at least one characteristic of the gas stream. The method 70 also includes calculating 74 a difference between the affected region of the affected waveform signal and a corresponding region of an original waveform signal, wherein the affected region and the corresponding region of the waveform signals have a sensitivity specific to the at least one characteristic of the gas stream. The method 70 also includes generating 76 a value for the at least one characteristic of the gas stream based on the calculated difference.

Figure 5:
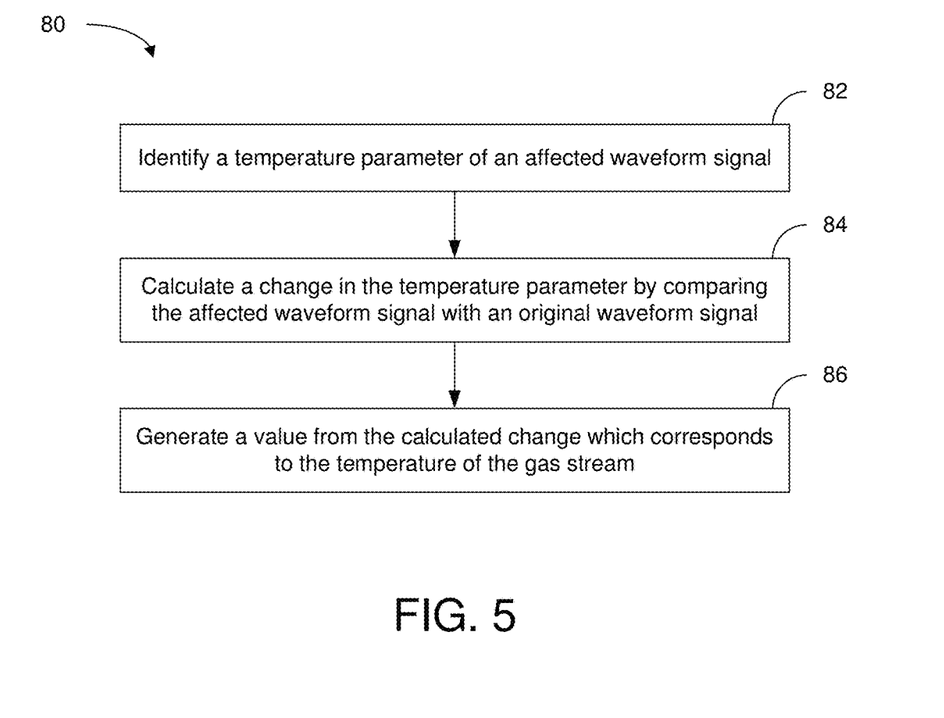
FIG. 5 depicts one embodiment of a flow chart diagram of a method for measuring temperature using voltage-current differential in the time-domain.

FIG. 5 depicts one embodiment of a flow chart diagram of a method 80 for measuring temperature using voltage-current differential in the time-domain. The method includes identifying 82 a temperature parameter of an affected waveform signal. The method also includes calculating 84 a change in the temperature parameter by comparing the affected waveform signal with an original waveform signal. The method also includes generating 86 a value from the calculated change which corresponds to the temperature of the gas stream.

It should be noted that at least some of the operations for the methods may be implemented using software instructions stored on a computer useable storage medium for execution by a computer. As an example, an embodiment of a computer program product includes a computer useable storage medium to store a computer readable program that, when executed on a computer, causes the computer to perform operations, including an operation to detect an affected waveform and compare the affected waveform against an original waveform to determine at least one characteristic of a gas stream.

Some embodiments described herein may include at least one processing device coupled directly or indirectly to memory elements through a system bus such as a data, address, and/or control bus. The memory elements can include local memory employed during actual execution of the program code, bulk storage, and cache memories which provide temporary storage of at least some program code in order to reduce the number of times code must be retrieved from bulk storage during execution.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Embodiments of the invention can take the form of an entirely hardware embodiment or an embodiment containing both hardware and software elements. In one embodiment, the invention is implemented in software, which includes but is not limited to firmware, resident software, microcode, etc. on a hardware device such as a processor, a memory device, or another device capable of storing non-transient signals and/or processing related signals.

Furthermore, embodiments of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The computer-useable or computer-readable medium can be an electronic, magnetic, optical, electromagnetic, infrared, or semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Input/output or I/O devices (including but not limited to keyboards, displays, pointing devices, etc.) can be coupled to the system either directly or through intervening I/O controllers. Additionally, network adapters also may be coupled to the system to enable the data processing system to become coupled to other data processing systems or remote printers or storage devices through intervening private or public networks. Modems, cable modems, and Ethernet cards are just a few of the currently available types of network adapters.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for temperature analysis of a gas stream, comprising:
  generating, by a signal generator, an original waveform;
  receiving, by a sensor, the original waveform;
  generating, by the sensor, an affected waveform signal representing temperature of a gas stream from the original waveform;
  identifying, by a processor, an affected region of the affected waveform signal corresponding to the temperature of the gas stream by comparing at least one portion of the affected waveform signal and the original waveform;
  calculating, by the processor, a voltage-current time differential between the affected region of the affected waveform signal and a corresponding region of the original waveform signal, wherein the affected region and the corresponding region of the waveform signals include a sensitivity specific to the temperature of the gas stream;
  generating, by the processor, a value corresponding to the temperature of the gas stream based on the calculated voltage-current time differential; and
  outputting, by the processor, the generated value.

2. The method of claim 1, wherein:
  the original waveform signal includes a reduced sensitivity to gas species within the gas stream;
  the sensor is disposed at least partially within the gas stream;
  the affected waveform signal is detected at the processor; and
  the value corresponding to the temperature of the gas stream is output at the sensor.

3. The method of claim 2, wherein outputting the value further comprises sending the value to the signal generator to adjust a subsequent original waveform signal.

4. The method of claim 1, wherein the sensor comprises a two-electrode sensor.

5. The method of claim 4, wherein electrodes of the two-electrode sensor are asymmetric.

6. The method of claim 5, wherein the asymmetric electrodes comprise a first electrode comprising gold (Au) and a second electrode comprising platinum (Pt).

7. A system for temperature analysis of a gas stream, comprising:
  a signal generator configured to generate an original waveform;
  a sensor configured to:
    receive the original waveform; and
    generate, from the original waveform, an affected waveform signal representing temperature of a gas stream; and
  a processor configured to:
    identify an affected region of the affected waveform signal corresponding to the temperature of the gas stream by comparing at least one portion of the affected waveform signal and the original waveform;
    calculate a voltage-current time differential between the affected region of the affected waveform signal and a corresponding region of the original waveform signal, wherein the affected region and the corresponding region of the waveform signals include a sensitivity specific to the temperature of the gas stream;

generate a value corresponding to the temperature of the gas stream based on the calculated voltage-current time differential; and output the generated value.

8. The system of claim 7, wherein:

the original waveform signal includes a reduced sensitivity to gas species within the gas stream;

the sensor is disposed at least partially within the gas stream;

the affected waveform signal is detected at the processor; and the value corresponding to the temperature of the gas stream is output at the sensor.

9. The system of claim 8, wherein the processor, when outputting the value, is further configured to send the value to the signal generator to adjust a subsequent original waveform signal.

10. The system of claim 7, wherein the sensor comprises a two-electrode sensor.

11. The system of claim 10, wherein electrodes of the two-electrode sensor are asymmetric.

12. The system of claim 11, wherein the asymmetric electrodes comprise a first electrode comprising gold (Au) and a second electrode comprising platinum (Pt).

* * * * *